United States Patent [19]

aus der Funten et al.

[11]  4,400,533
[45]  Aug. 23, 1983

[54] METHOD OF PREPARING D,L-PHENYLALANINE

[75] Inventors: Helmut aus der Funten, Mondorf; Klaus Schrage, Uthweiler, both of Fed. Rep. of Germany

[73] Assignee: Dynamit Nobel Aktiengesellschaft, Troisdorf Bez. Cologne, Fed. Rep. of Germany

[21] Appl. No.: 346,824

[22] Filed: Feb. 8, 1982

Related U.S. Application Data

[63] Continuation of Ser. No. 172,727, Jul. 28, 1980, abandoned.

[30] Foreign Application Priority Data

Aug. 1, 1979 [DE] Fed. Rep. of Germany ....... 2931224

[51] Int. Cl.$^3$ .............................................. C07C 99/00
[52] U.S. Cl. .................................................... 562/443
[58] Field of Search ................................ 562/443, 575

[56] References Cited

U.S. PATENT DOCUMENTS 3,867,435   2/1975   Diamond et al. ................... 562/443
4,073,804   2/1978   Hearon et al. ...................... 562/575

Primary Examiner—James H. Reamer
Attorney, Agent, or Firm—Sprung, Horn, Kramer & Woods

[57] ABSTRACT

A process for preparing an alkali salt of d,l-phenylalanine and the free acid thereof is disclosed. According to the invention an alkali salt of phenylpyruvic acid is reacted at elevated pressure with hydrogen and ammonia in the presence of a noble metal catalyst of Group VIII. If the acid is desired it is obtained by acidification of the corresponding salt.

11 Claims, No Drawings

METHOD OF PREPARING D,L-PHENYLALANINE

This is a continuation, of application Ser. No. 06/172,727, filed July 28, 1980, now abandoned.

BACKGROUND

The invention relates to a method of preparing d,l-phenylalanine (PA) by the aminating catalytic hydrogenation of alkali salts of phenylpyruvic acid to the corresponding salts of phenylalanine.

It is known to prepare d,l-PA by the aminating catalytic hydrogenation of phenylpyruvic acid (abstract in A. Meister, Biochemistry of the Amino Acids, 2nd ed., New York - London 1965). The yield of the aminating hydrogenation with noble metal catalysts amounts, however, to only 62 to 67% of d,l-PA (F. Knoop, H. Oesterlin, Hoppe Seylers Zeitschrift fuer Physiologische Chemie 148, 311 (1925), 170, 187 and 195 (1928), E. Reimann, D. Voss, Arch. Pharm. 309, 983 (1976)).

The necessary purification involves an additional reduction of the yield, so that industrial production of PA from phenylpyruvic acid has not been possible.

The subject matter of the invention is a method of preparing alkali salts of d,l-phenylalanine, which is characterized in that an alkali salt of phenylpyruvic acid is reacted with hydrogen and ammonia at elevated pressure in the presence of a noble metal catalyst of Group VIII of the Periodic Table.

In accordance with the method of the invention, the yields of alkali salt of PA exceed 90% of the theory. The salts of PA have the advantage of making possible numerous reactions, e.g., to the esters, in a more simple manner than the free PA, and they often result in better yields. An additional advantageous possibility is the use of the alkali salts directly for the enzymatic separation of the optical antipodes and isolation of the physiologically valuable l-phenylaline. In accordance with DE-OS No. 2,741,081, the alkali salts of, for example d,l-PA can be transformed in aqueous solution with ketene to the N-acetylamino acid alkali salts, and to l-phenylalanine by subsequent enzymatic cleavage. Also, the free d,l-PA is easy to obtain in a known manner. The alkali salts of phenylpyruvic acid are mainly the Na+, K+ or Li+ salts, of which the lithium salts are preferred. The free d,l-PA can be obtained from the salt thereof by acidification of the salt with an acid, e.g., H Cl.

The noble metals of Group VIII of the Periodic Table of the elements can be used as catalysts, namedly Ru, Rh, Pd, Os. Ir and Pt, of which Rh, Pd and Pt are preferred and Pd is greatly preferred.

The noble metal catalyst can be used in its metallic form or deposited on a support. Supported catalysts, especially those on supports such as active charcoal, $CaCO_3$, $Al_2O_3$ or kieselgur, are used preferentially. A greatly preferred form of the method is the use of palladium catalysts on charcoal, which are made commercially by Degussa, Engelhard Ind. GmbH, Hannover, and Doduco et al., in the form of a 3 to 6% palladium, by weight, on charcoal. The pressure is to be between 10 and 200 Bar, preferably between 30 and 100 bar.

The reaction temperature is between 10° and 150° C. preferably between 20° and 80° C. The pressure is at least 300 bar and preferably up to 200 bar with a preferred range of 10 to 100 bar.

Solvents are to be those which are inert under the reaction conditions. Hydrophilic solvents are preferred, because thus the water formed in the reaction is taken up in a homogeneous phase. Preferred solvents are alcohols of the aliphatic or cycloaliphatic series with 1 to about 10 carbon atoms. Methanol, ethanol, cyclohexanol and ethylene glycol are especially preferred. The reaction time can be varied between 2 and 6 hours. The amount of hydrogen is to be at least stoichiometric with respect to the transformation. The reaction pressure is sustained by the input of hydrogen during the reaction, until the end of the reaction is indicated by the fact that no more hydrogen is being consumed. The amount of the ammonia must be at least the stoichiometric amount, and can amount to 1 to 30 times, preferably 10 to 25 times the stoichiometric amount. A still greater excess does not have a negative effect, but it is avoided for economical reasons.

In the working up of the reaction mixture, the catalyst is filtered out and the solid product is obtained by removing the excess ammonia and solvent.

The alkali salts of PA prepared by the method of the invention are valuable chemical intermediates for the production of pharmaceutical products and active substances for the animal feed industry.

EXAMPLES

EXAMPLE 1

A 20-liter lifting magnetic stirrer autoclave is charged under nitrogen with 200 g of palladium charcoal catalyst (noble metal content 5 wt-%), 1000 g of phenylpyruvic acid lithium salt (moisture content 12.7%, corresponding to 5.2 moles effective) and 7900 g of methanol. The closed autoclave is repeatedly purged with nitrogen and hydrogen, and then 4 liters of liquefied ammonia and 50 bar of hydrogen are pumped in. After the stirrer is started up, the temperature rises to 37° to 40° C. and the pressure decreases. By the repeated addition of hydrogen the pressure is maintained between 45 to 50 bar in the 45°–47° C. temperature range, and the reaction is continued for three hours. In the after-reaction phase of one hour, the pressure remains virtually the same. The autoclave is cooled down to room temperature, and the pressure is relieved down to 5 bar, and at this pressure the catalyst is separated from the solution by means of a pressure filter. The solution is concentrated at about 50° C. in a rotary film evaporator to remove ammonia and methanol until about 90% of the aboumt of solvents put in have been evaporated out. The reaction product is brought to room temperature, filtered, washed with a little cold methanol, and dried. Yield of d,l-PA lithium salt 774 g (moisture content 2.3%), M.P. 229° C. By concentrating the filtrate, an additional 48.5 g of lithium salt is obtained, so that the total yield amounts to 804.5 g (4.73 moles=91% of the theory). In the salt, the lithium content amounts to 4.09 wt-%. (theoretical content 4.08%).

EXAMPLE 2

If the procedure of Example 1 is repeated and the hydrogenation is performed in the presence of 2.8 liters of ammonia while the composition is otherwise the same, and the temperature is 65° C. and the hydrogen pressure 25 bar, one obtains after similar processing 791.2 grams of d,l-phenylalanine lithium salt containing 4.1 wt-% of lithium and having a melting point of 227° C. Yield 89.5% of the theory.

EXAMPLE 3

If a procedure similar to Example 1 is followed and the residue obtained after filtering out the catalyst and concentrating the filtrate in the rotary film evaporator is dissolved in 6 liters of water and acidified with hydrochlroic acid to pH 5.8, and if the precipitated d,l-phenylalanine is filtered out, washed with water until no $Cl^1$ ions can be detected, and dried in the vacuum dryer at 100° C., 72.5 g of d,l-phenylalanine is obtained, with a melting point of 281° C. Yield 84.6% of the theory).

EXAMPLE 4

By proceeding as in Example 1, but using the equivalent amount (a) of the sodium salt of phenylpyruvic acid and (b) of the potassium salt, a corresponding yield is obtained of the sodium and potassium salts, respectively, of the d,l-phenylalanine.

What is claimed is:

1. A method for preparing an alkali salt of d,l-phenylanine, which comprises containing an alkali salt of phenylpyruvic acid with hydrogen and ammonia at elevated pressure in the presence of a noble metal catalyst of Group VIII of the Periodic Table.

2. A process according to claim 1, wherein the noble metal is palladium.

3. A process according to claim 1, wherein ammonia is present in the reaction mixture in an amount of 1 to 30 times the stoichiometric amount.

4. A process according to claim 1, wherein the pressure is 10 to 200 bars.

5. A process according to claim 1, wherein reaction is conducted at a temperature of 10° to 150° C.

6. A process according to claim 1, wherein the alkali metal salt is lithium.

7. A process according to claim 1, wherein thereafter the so-prepared alkali metal salt of d,l-phenylalanine is converted to the free acid by contacting the salt with an acid.

8. A process according to claim 1, wherein
   a. the noble metal is palladium
   b. the temperature is 20°–80° C.
   c. the pressure is 10–100 bar.

9. A process according to claim 6, wherein
   a. the noble metal is palladium b. the temperature is 20°–80° C.
   c. the pressure is 10–100 bar.

10. A process according to claim 8, wherein the reaction is carried out for between two and six hours.

11. A process according to claim 9, wherein the reaction is carried out for between two and six hours.

* * * * *

UNITED STATES PATENT AND TRADEMARK OFFICE
CERTIFICATE OF CORRECTION

PATENT NO. : 4,400,533
DATED : August 23, 1983
INVENTOR(S) : HELMUT AUS DER FÜNTEN et al It is certified that error appears in the above-identified patent and that said Letters Patent is hereby corrected as shown below:

TITLE                    Delete "D,L" and insert --D,1--

Col. 2, line 50     Delete "aboumt" and insert --amount--

Col. 3, line 25 (claim 1)     Delete "phenylanine" and insert --phenylalanine--

Col. 3, line 25 (claim 1)     Delete "containing" and insert --contacting--

Signed and Sealed this

Eighth Day of November 1983

[SEAL]

Attest:

GERALD J. MOSSINGHOFF

Attesting Officer      Commissioner of Patents and Trademarks